United States Patent [19]

van Staaveren

[11] Plant 4,599

[45] Oct. 7, 1980

[54] ALSTROEMERIA PLANT NAMED YELLOW KING

[76] Inventor: M. C. van Staaveren, 30, Hornweg, 1432 GM Aalsmeer, Netherlands

[21] Appl. No.: 32,677

[22] Filed: Apr. 23, 1979

[51] Int. Cl.[3] ..... A01H 5/00
[52] U.S. Cl. ..... Plt./68
[58] Field of Search ..... Plt./68

*Primary Examiner*—Robert E. Bagwill
*Assistant Examiner*—James R. Feyrer
*Attorney, Agent, or Firm*—Chas. W. Rummler

[57] ABSTRACT

A new variety of alstroemeria plant characterized by the brilliant yellow color of its unusual and prolifically produced blooms, each of which is presented on a long, strong peduncle; and by the relatively long-lasting quality of its flowers both on the plant and as cut flowers.

1 Drawing Figure

BACKGROUND OF THE INVENTION

This new variety of alstroemeria originated as a seedling resulting from breeding efforts carried on by me at Aalsmeer, Holland, since 1971 with the object of obtaining a wider color range and better wintertime production. This seedling resulted from my crossing Aur. 4×1198-1, unnamed varieties maintained by me for breeding purposes, and was selected for propagation and trial because of its brilliant yellow color and the relatively large size of its flowers. This plant was asexually reproduced by me at Aalsmeer, Holland; and subsequently, this plant was propagated through successive generations by dividing root stocks. This propagation demonstrated that the distinctive characteristics of the new plant hold true from generation to generation and appear to be firmly fixed. Propagation of this plant is now being carried on by root stock division at Aalsmeer, Holland.

DESCRIPTION OF THE DRAWING

My new variety of alstroemeria is illustrated by the accompanying full color photographic drawing, which shows the form and color characteristics of the flowers as nearly true as it is reasonably possible to obtain by conventional professional photographic procedures and processes.

DESCRIPTION OF THE NEW PLANT

The following is a detailed description of this new variety of alstroemeria with color designations according to The R.H.S. Colour Chart published by The Royal Horticultural Society of London, England.

THE PLANT

Origin: Seedling.
Parentage: Aur. 4×1198-1, unnamed varieties maintained for breeding purposes.
Classification:
*Botanic.*—Alstroemeria.
*Commercial.*—Alstroemeria for cut flower production.
Form: Herbaceous, sturdy and upright.
*Height.*—About 1.5 to 2.0 meters at maturity.
Growth: Vigorous.

Root stock: Tuberous, producing 40 or more buds during the year from which flower stalks grow in various stages of development during the course of the year.
Branching: Each flower stalk branches at the top as an umbel to provide 4 to 8 flower bearing raceme stems which grow outward from about 12 cm. as buds and flowers develop.
Foliage: Quantity — abundant with 30 to 40 leaves.
*Form of leaf.*—Long and narrow with acuminate apex.
*Texture.*—Soft.
*Color.*—Dark green.

THE BUD

Form: Pear shaped at the beginning, becoming long pointed just before opening.
Size: About 2.5 cm. long at opening.
Opening rate: The bud opens slowly.
Peduncle: Strong.

THE FLOWER

Blooming habit: Recurrent, early Spring, midseason and Fall, with more-or-less continuous, profuse production of flowers during each blooming season.
Size: Medium.
*Diameter.*—About 5.5 cm.
*Depth.*—About 4.5 cm.
Shape: Generally funnel-like.
Borne: Singly on a long peduncle.
Petalage: Number of petals — 6.
*Arrangement.*—2 concentric circles of 3 each.
*Form.*—Wide elliptic, slightly serrated at the top.
*Texture.*—Soft.
*Appearance.*—Shiny.
*Color.*—Outer petals — 17B plus 14A-B. Inner petals — 14A plus 17B. Reverse side of petals — 17B-C.
Effect of weather: Hot weather causes paler color.
Persistence: The flowers hang on and dry.
Lasting quality:
*On the plant.*—14 days for each flower.
*As a cut flower.*—9 days for each flower.
Discoloration: The flower color darkens gradually as the flower ages.

REPRODUCTIVE ORGANS

Stamens:
*Number.*—Six.

*Arrangement.*—One opposite each petal.

*Anthers.*—Length about 8 mm.

Pistils: Only one.

*Style.*—about 3.5 cm. long.

This new variety of alstroemeria plant is distinguished by the bright yellow color of its blooms and the broken lines of dark brown pencil-stripe spots which extend lengthwise of the inner, nectar-bearing petals. This plant is also distinguished by its vigorous growth and its continuous production of flowers borne on strong, upright, raceme stems which grow in simple umbel arrangement at the end of each stalk.

I claim:

1. A new and distinct variety of alstroemeria plant substantially as herein shown and described, characterized by the distinctive darkish yellow overall coloring of its flower petals, its substantially continuous production of flowers, and the long-lasting quality of the flowers both on the stem and as cut flowers.

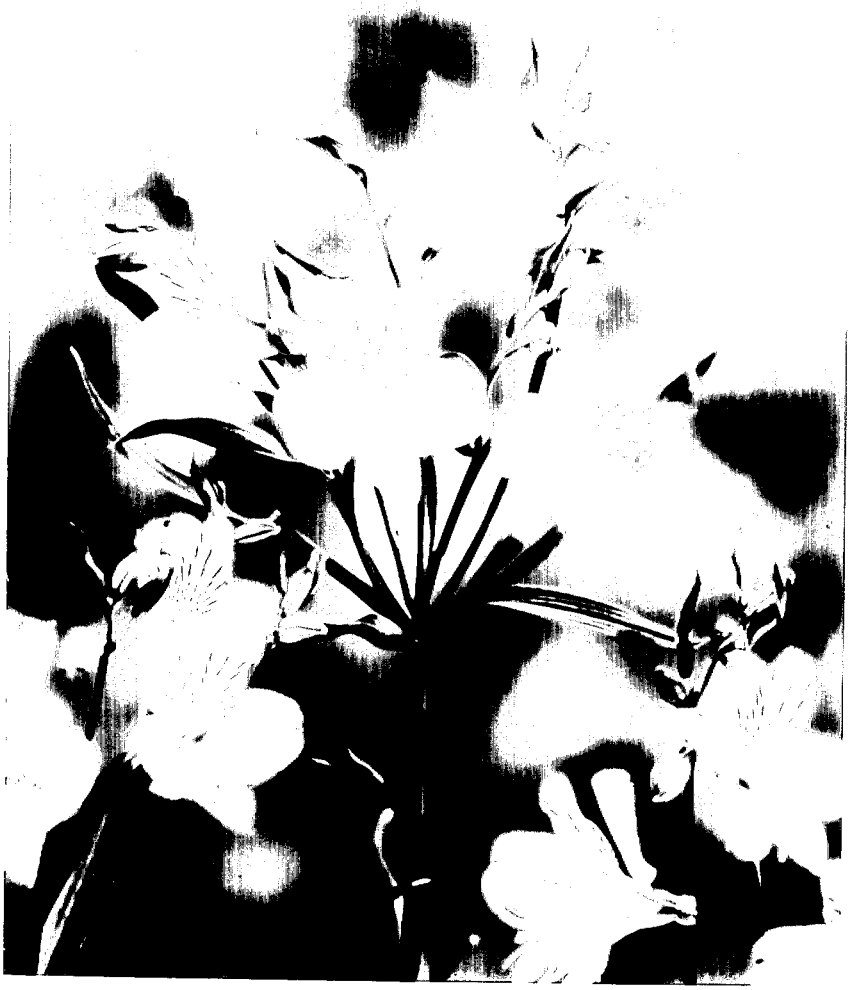

* * * * *